United States Patent
O'Leary

(10) Patent No.: US 6,631,852 B1
(45) Date of Patent: Oct. 14, 2003

(54) VAPOR DISPENSING DEVICE

(75) Inventor: Nicholas O'Leary, Slough (GB)

(73) Assignee: Reckitt Benckiser (UK) Limited, Slough (GB)

( * ) Notice: Subject to any disclaimer, the term of this patent is extended or adjusted under 35 U.S.C. 154(b) by 0 days.

(21) Appl. No.: 09/807,795

(22) PCT Filed: Oct. 22, 1999

(86) PCT No.: PCT/GB99/03424
§ 371 (c)(1),
(2), (4) Date: Jul. 9, 2001

(87) PCT Pub. No.: WO00/24434
PCT Pub. Date: May 4, 2000

(30) Foreign Application Priority Data

Oct. 22, 1998 (WO) .................. PCT/IB98/01701

(51) Int. Cl.[7] .................. A24F 25/00; A61L 9/04
(52) U.S. Cl. .................. 239/60; 239/54; 239/55; 239/57
(58) Field of Search .................. 239/60, 54, 55, 239/57, 34, 51.5; 424/76, 60, 43, 70.1; 523/102, 4

(56) References Cited

U.S. PATENT DOCUMENTS

| | | | | |
|---|---|---|---|---|
| 3,804,331 A | * | 4/1974 | Levey | 239/59 |
| 4,250,165 A | * | 2/1981 | Foley | 424/76.1 |
| 4,293,095 A | * | 10/1981 | Hamilton et al. | 239/35 |
| 4,362,841 A | | 12/1982 | Minatono et al. | 524/531 |
| 5,136,684 A | * | 8/1992 | Lonker et al. | 392/392 |
| 5,749,519 A | * | 5/1998 | Miller | 239/44 |
| 5,780,527 A | | 7/1998 | O'Leary | 523/102 |

FOREIGN PATENT DOCUMENTS

| | | | | |
|---|---|---|---|---|
| EP | 0 028 852 A1 | 5/1981 | | A61L/9/12 |
| FR | 2 455 068 | 11/1980 | | C08L/35/00 |
| GB | 2 039 740 A | 8/1980 | | A61L/9/12 |
| WO | WO97/35626 | 10/1997 | | A61L/9/04 |

* cited by examiner

Primary Examiner—Davis Hwu
(74) Attorney, Agent, or Firm—Fish & Richardson P.C.

(57) ABSTRACT

A device for diffusion of an active volatile substance into ambient air or closed spaces comprising a solid casing or housing and a solid carrier containing said volatile substance. The solid carrier is arranged in at least one recess formed in the housing, said recess having a depth and a width which are chosen in relation to the composition of the solid carrier so that the ratio of the evaporation surface of the solid carrier to the mass of the solid carrier is such that a substantially constant vapor release rate and total evaporation of said active volatile substance during the active lifetime of the device is obtained. The recesses can be of various geometrical shapes in order to give a pleasant appearance. The active volatile substance can be a perfuming, deodorizing, sanitizing composition or an insect repellent.

21 Claims, 2 Drawing Sheets

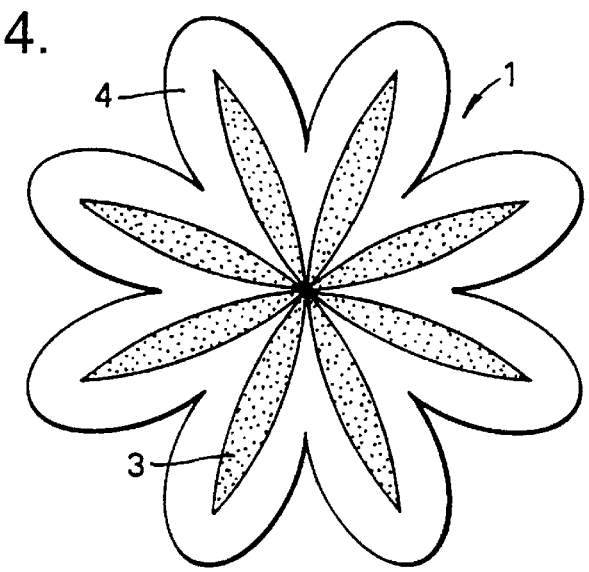
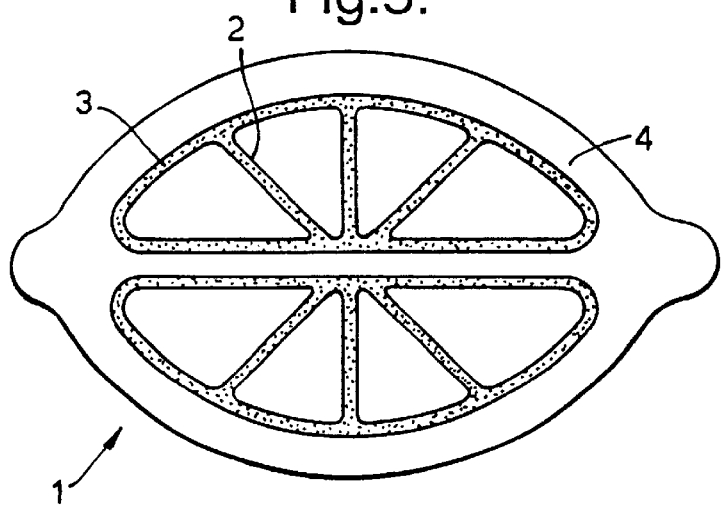
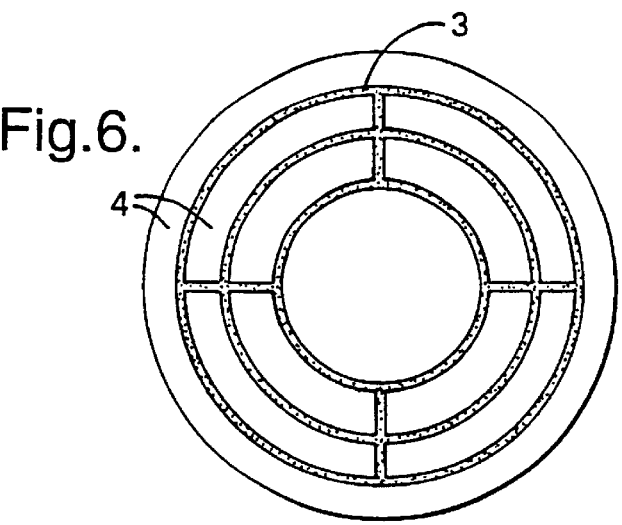

VAPOR DISPENSING DEVICE

BACKGROUND OF THE INVENTION

The present invention relates to the field of perfumery. It relates, more particularly, to a device for diffusing perfume into the surrounding air. The device of the invention, however, can also be used for the diffusion of other active volatile agents, such as insect repellents, deodorizing or sanitizing agents, amongst others.

The use of various devices for the diffusion of volatile compounds, for example perfumes, sanitizing agents, insect repellents, and the like, has become more and more current in recent years. For example, air-freshening devices or deodorizers are currently used in practically all households to mask bad odours or to impart fragrances to the ambient air. The known devices used for the diffusion of volatile compounds into the surroundings make use of various principles. As an example, one can mention here dispersing devices of the spray type, aerosols or mechanical. Other examples include plastic packing elements enclosing the active ingredients in liquid form. Typically, the diffusion of the active ingredient takes place through membranes permeable to the vapours of said ingredient.

One class of systems capable of diffusing active volatile ingredients and which are of relevance with respect to the present invention are solid state devices consisting of solid materials or carriers impregnated with an active ingredient. Such devices may be formed of various materials which are capable of absorbing the ingredient and subsequently releasing it in a more or less controlled manner. Examples of such known materials include gels, such as agar-agar or sodium stearate gels, synthetic polymer resins, or blocks of mineral material, e.g. plaster or silica. It is even possible, for some purposes, to have active ingredients absorbed on paper or cardboard in order to obtain a more or less solid carrier device for diffusing the volatile ingredient thus absorbed. Often, solid devices are designed to be non-wetting, i.e. to be capable of effectively retaining the liquid active volatile material and only allowing the diffusion of the vapours of said material.

Solid state air-freshener devices have the advantage that they are easy to handle and may be shaped into various forms adapted to the customers' needs and desires. The devices can for example be in the form of a solid block of a particular shape, e.g. a figure or a geometrical form, and be used as such. A material often used for such devices is plaster, allowing an easy shaping of the raw material into the desired form.

Solid state devices can also be placed into a housing in which they are typically covered by a lid or a grill having openings to allow for communication between the surrounding air and the perfumed solid block, or they can be arranged between two grills. In these applications, the solid perfumed block is covered by said lid or said grill and is sometimes invisible from the outside of the packing. Unlike the unhoused air-fresheners, the appearance of the latter air-freshening devices is that given by the housing or the grill, and it is therefore not necessary, or not even possible, to shape the solid block into a particular form to cause an aesthetic impression.

Solid block perfuming devices, however, generally have the drawback that the vapour release rate is not constant, but drops dramatically within the lifetime of the product. Furthermore, often the device is already exhausted, i.e. no longer diffuses sufficient active ingredient, in spite of the fact that considerable amounts of active ingredient still remain in the core of the block. This residual perfume, retained by the material of the block, is therefore entirely lost.

The object of the present invention is to provide a solid air-freshening device for diffusing volatile substances, e.g. perfumes, insect repellents, deodorizing or sanitizing agents, which is capable of diffusing said volatile substances at a relatively constant rate throughout the lifetime of the device. Furthermore, the devices of the invention are capable of releasing practically their entire content of volatile substance within their effective lifetime, such that very little active ingredient will be retained as a residue.

SUMMARY OF THE INVENTION

Accordingly, the present invention provides a device for the diffusion of an active volatile substance into ambient air or closed spaces comprising a solid casing or housing and a solid carrier containing said volatile substance wherein said solid carrier is arranged in at least one recess formed in the housing, the at least one recess having a depth and a width which are chosen in relation to the composition of the solid carrier containing the active substance so that the ratio of the evaporation surface of the solid carrier to the mass of the solid carrier disposed within the said recess is such that a substantially constant vapour release rate and total evaporation of said active volatile substance during the active lifetime of the device is obtained.

The term "lifetime" in relation to the diffusion device of the present invention is used here to designate the period of time during which the device diffuses an amount of active ingredient sufficient to be effective, i.e. which, for example, can be perceived in the case of perfumes, or can remain active as insect repellent, deodorizing or sanitizing agent, and the like.

BRIEF DESCRIPTION OF THE DRAWINGS

FIGS. 4 to 6 represent other embodiments of the device according to the invention in the form of, respectively, a flower, a lemon and a disc.

DETAILED DISCLOSURE

Figure 1:
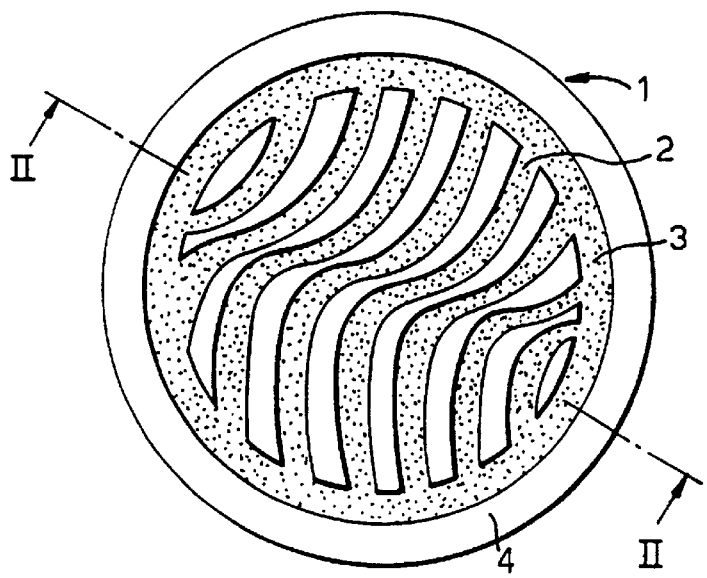
FIG. 1 is a plan view of an embodiment of a device according to the invention.

The solid casing or housing of the device of the invention can be formed of any convenient material into which small-sized recesses can be cut or moulded and which is adapted to be used as a bulk article. The material should thus be nontoxic and retain its form upon storage or use. The material can, of course, show a certain flexibility. An important criterion for the choice of the appropriate material is its compatibility with the solid carrier containing the volatile substance, such that the latter remains lodged in the recesses of the housing even after complete evaporation of the volatile substance.

Preferred materials for the housing or casing include wood, mineral materials (e.g. plaster), glass, or synthetic polymers (e.g. acrylic and methacrylic polymers, polystyrene, polyesters, phenolic resins or silicones). The solid housing may have any geometrical shape, for example a cylinder, a prism, a pyramid, a tetrahedron, a cube or a diamond. The geometrical shape is preferably chosen to have a pleasant appearance.

According to a preferred embodiment of the invention, the housing or casing is formed as a single block, having two substantially parallel faces, the lower face being flat, and the recesses being cut or moulded into the upper face of the block.

The materials which can be used to form the solid carrier incorporating the volatile substance are the usual materials known in the art as being appropriate carriers for the perfumes, or insect repellent, deodorizing or sanitizing agents or the like used according to the present invention. These carriers are capable of incorporating a considerable amount of active substance, typically between about 5 and 90% of their total weight, and they are capable of retaining the active substance, i.e. the latter will not flow out of the carrier material in any considerable amount, being intended to be released in the gaseous state from the carrier material into the surroundings of the air freshener.

Preferably, the solid carrier will be of a material capable of adhering to the housing or casing by itself. Whenever the carrier is made of a material which does not adhere sufficiently to the chosen housing, it may be made to stay on the housing by means of e.g. an appropriate glue or polymer of synthetic or natural origin.

Non-limiting examples of appropriate carriers include plaster, silica, carboxymethylcellulose, wax-like materials (such as, for example, stearates or paraffins), alginates, carrageenans (such as, for example, agar-agar), paper, cardboard, synthetic polymers [such as, for example, polyacrylates, polymethacrylates or polyurethanes, polyethylene, ethylene-ethylacrylate copolymer, ethylene-vinyl acetate copolymer, a polyamide, a polyether block amide elastomer (e.g. Pebax®; origin: Elf Atochem)], polymer hydrogels (such as, for example, those disclosed in FR-A-2455068 or U.S. Pat. No. 4,362,841), or an hydrous polymer gels.

A preferred class of materials for the solid carrier incorporating the volatile substance are anhydrous gels such as those described in U.S. Pat. No. 5,780,527 which are formed via the cross-linking of a functionalised liquid polymer selected from maleinised polybutadiene or maleinised polyisoprene, or a copolymer consisting of ethylene and maleic anhydride, with a cross-linking agent which possesses one or more complementary functional groups, in the presence of a perfume, deodorizing or sanitizing base or of a surfactant agent. In a preferred embodiment, a functionalised liquid polymer selected from maleinised polybutadiene of molecular weight 5,000–20,000 or maleinised polyisoprene of molecular weight 200,000–500,000 is used. Suitable cross-linking agents include dihydroxypolybutadiene, ethoxylated or propoxylated primary fatty amines, alkylpropyldiamines having an ethoxylated or propoxylated higher aliphatic chain, diethanolamine, diethylenetriamine and polyoxyalkyleneamines, in particular polyoxyalkylenediamines and -triamines. It is advantageous to use the functionalised liquid polymer and the cross-linking agent in a molar ratio of approximately 1:1. In the most preferred embodiment, the anhydrous gel results from the in situ cross-linking between a functionalised liquid polymer and a cross-linking agent consisting of either an oleylamine having 2 ethylene oxide units per molecule, a cocoamine having 5 ethylene oxide units per molecule, or polyoxyalkylenediamine or -triamine.

The gels which are obtained according to the above description are capable of absorbing large amounts of an active, volatile ingredient, e.g. a perfume, an insect repellent, a deodorizing or sanitizing base or the like.

The above-cited polymeric materials are all commercially available. As examples for maleinised polybutadiene or polyisoprene, one can cite the products known widely under the name of "Lithene®" [origin: Revertex Ltd]. Amongst the different qualities of available Lithene®, good results have been obtained by using "Lithene® N4-9000 1OMA" [origin: Revertex Ltd]; 9000 stands for the molecular weight of polybutadiene before maleinisation, whilst 1OMA indicates the degree of maleinisation—in this case 10 parts of maleic anhydride per 100 parts of polybutadiene (about 9.1%)—Lithene N4-B-1OMA, has also proven to be particularly useful.

As examples of cross-linking agents, one can cite the following agents alkylpropyldiamines having an ethoxylated or propoxylated higher aliphatic chain: products available under the name Dicrodamet (origin: Croda Chemicals Ltd)

ethoxylated or propoxylated primary fatty amines: Crodamet (origin: Croda Chemicals Ltd), in particular Crodamet 02 (oleylamine having 2 ethylene oxide units per molecule) and Crodamet C5 (cocoamine having 5 ethylene oxide units per molecule)

polyoxyalkylenediamines: Jeffamine® D and ED series (origin: Huntsman Corporation), in particular Jeffamine® D-400, Jeffamine® EDR-148 and Jeffamine® D2000 polyoxyalkylenetriamines: Jeffamine® T-403.

One can also cite polybutadiene having a hydroxylic function known as HFPB (origin: Revertex Ltd) which gelifies when admixed with maleinised polybutadiene. Sometimes, the use of specific catalysts allows better control of the gel formation and, to this end, there are used tertiary amines (e.g.: DAMA 1010, a dialkylamine; origin: Albemarle SA). Mixtures of Hycar CTBN 1300×21, which is an amine terminated liquid butadiene/acrylonitrile copolymer (origin: B.F. Goodrich), and maleinised polybutadiene are also suitable.

As cited above, these anhydrous gels which are particularly adapted to be used in the present invention, are described in U.S. Pat. No. 5,780,527 (assignee: Firmenich SA).

An important feature of the present invention are the small-sized recesses formed in the solid casing or housing and containing the carrier holding the active substance. In order to allow the desired constant vapour release and complete evaporation of the active substance, the recesses must be of a sufficiently small size and have an appropriate depth and width. In other words, the solid carrier arranged within the recess and containing the active substance must have a high evaporation surface/mass ratio to allow sufficiently rapid diffusion of the active substance which it incorporates to the surface of the device, so as to ensure the constant and regular evaporation of said substance. However, the ratio between the evaporation surface and the mass of the solid element should not be too high, in order to prevent a "burst-like" and rapidly declining release of the active substance, i.e. the recess must not be too large or too shallow.

When in the above there is made mention of the evaporation surface/mass ratio, one can of course also use the evaporation surface/volume ratio in order to describe the same relationship, both values being easily convertible into each other via the density of the respective material.

A person skilled in the art will recognize that the appropriate size for the recess has to be selected as a function of, for example, the nature of the material of the solid carrier and its porosity (which may vary for a given material according to the mode of preparation), the amount of active ingredient and its volatility, or the interaction between the solid carrier material and the active substance. All of these parameters can have an impact on the efficiency of diffusion of the volatile substance and the appropriate size of the recesses can thus be readily determined on a case by case basis.

Recesses of many different forms can be used in the device of the invention. As non-limiting examples, there are cited groove-, round-, oval-, square-, diamond-, star- or triangular-shaped recesses. The recesses may have a constant or variable depth and/or a constant or variable width. Generally, the geometrical form of the recesses is not critical for the devices of the present invention, as long as these are of the appropriate size, as discussed above. Typical shapes can be labyrinth- or serpentine-like for example, without any vertical walls or separations within the hollow volume of the recess.

When the device of the invention comprises several recesses, these can be arranged so as to be isolated from each other or to be arranged in a communicating manner. According to a preferred embodiment of the invention, the solid support comprises several communicating grooves.

It is clear that for a recess of a given size, the evaporation surface/mass ratio is considerably influenced by the height up to which the said recess is filled with the perfume-containing carrier. In a preferred embodiment of the invention, the recess or recesses are only partially filled with the solid carrier. The customer will thus not contact the carrier during normal use of the device. In order to avoid such contact, the recesses of the device of the invention are small in shape and filled up to a degree which will not allow a user to touch the solid carrier containing the active components with his fingers. This applies likewise to adults' and babies' fingers, and in this manner the device of the invention has the advantage of complying with a variety of safety regulations.

The recesses may be shaped on only one surface of the support or, alternatively, on several of these, e.g. two opposite surfaces or faces of the support. Likewise, the recesses may be blind recesses or extend through the entire thickness or width of the casing or housing. Furthermore, multipiece devices may be formed, for example two single face devices which are attached back to back.

The recesses of the housing of the present invention can be filled up partially or entirely with the solid carrier or element containing the volatile substance, via various methods which are known in the art. For example, the solid carrier material can be pressed mechanically into the recesses after having been prior impregnated with the volatile substance, e.g. perfume. This will be appropriate in the case of paper or cardboard being used as the carrier. Other methods include pouring, moulding or extrusion, which methods will be mainly applied when the carrier holding the volatile active substance is made of a material which originally is in the liquid state and is capable of solidifying or gelling after having been introduced into the recesses. Materials showing this property are for example plaster or synthetic polymers, in particular the polymers disclosed in U.S. Pat. No. 5,780,527.

The overall surface of the solid carrier which is exposed to the air, after arrangement in the recess or recesses of the solid support, typically ranges from about 5 to 100 $cm^2$, preferably from about 10 to 50 $cm^2$. Typical amounts of solid element range from about 2 g to 50 g, preferably from about 3 g to 30 g. The precise values for the abovementioned surface area and the amounts of solid element depend, amongst others, on the size of the diffusion device, the properties of the material of the housing or casing, e.g. its porosity or how much active ingredient it can incorporate, and the desired effect of the device.

In the case of the carrier materials as disclosed in U.S. Pat. No. 5,780,527, the typical amount of carrier is from about 2 g to 20 g, preferably from about 3 g to 10 g.

A particular advantage of the device of the present invention lies in the possibility of forming recesses of various forms into said housing or casing or arranging these in various manners. In this way, the present invention allows the formation of geometrical shapes or arrangements on one or more of the faces or surfaces of the support designed to be exposed to the air, so as to give a pleasant and aesthetic impression to the user. The device can also be adapted to various tastes and preferences. The solid carrier containing the volatile substance plays an active role in the visual impression imparted to the consumer. However, unlike in other applications in which a solid, volatile substance containing material is shaped into a certain geometrical form and used as such as a diffusion device, the present invention makes it possible to obtain devices which are freely shaped as desired, but in which the user can be protected from touching, or getting into contact with, the solid carrier of the volatile substance even when the device is activated. As well as random geometric shapes, symmetrical patterns may be formed or a logo, brand name or word could be formed by the recesses of the device.

When the diffusion device of the present invention comprises the solid gel element disclosed in U.S. Pat. No. 5,780,527, the device has the further advantage that the gel can provide an end point indication of exhaustion of its activity, i.e. when all of the active substance has evaporated and the device no longer has any perfuming activity. This end point cue is provided by the shrinkage of the gel material, within the recess or recesses, which is perfectly visible. Often, also a cracking or tearing of the gel material is observed. This is particularly the case when the device of the invention comprises recesses in the form of grooves which are arranged in a communicating manner.

When the diffusion device of the present invention is unactivated, as for example during storage and before use, at least the surface in which the grooves were carved is covered by an appropriate material, impermeable to the vapours of the active substance, e.g. aluminum foil, in order to avoid evaporation of the active volatile substances. Upon activation of the device to diffuse the volatile substance, the aluminum foil or other protecting material, impermeable to the vapours of the latter, shall be removed.

As a perfume base there can be used in the device of the invention any composition currently used in perfumery. The latter can be made of discreet chemicals; more often, however, it will be a more or less complex mixture of volatile liquid ingredients of natural or synthetic origin. The nature of these ingredients can be found in specialized books of perfumery, e.g. in S. Arctander (Perfume and Flavor Chemicals, Montclair N.J., USA 1969) or similar textbooks of reference.

Although special mention has been made hereinabove of the perfuming effect exerted by the invention device, the same principles apply to the manufacture of analogous devices for the diffusion of deodorizing or sanitizing vapours, the perfume base being then replaced by a deodorizing composition, a bactericide, an insecticide, a repellent or even an attractant. By the term "sanitizing", we refer here not only to those substances which can enhance the degree of acceptance of the surrounding air by an observer, but also to those substances which can exert an attractant or repellent effect towards certain species of insects, for instance towards houseflies or mosquitoes, or else which can have bactericide or bacteriostatic activity. It goes without saying that mixtures of such agents can also be used.

The invention will now be described in greater detail by way of the following non-limiting examples, in which the abbreviations have the meanings known in the art and the temperatures are indicated in degrees centigrade, and with reference to FIGS. 1 to 3.

EXAMPLE 1

Manufacture of the Housing or Casing

A cylindrical, one-piece block having a flat lower face and an upper face provided with at least one recess was manufactured from polymethylmethacrylate (PMMA) by a method known in the art such as, for example, casting, moulding, injection-moulding, or other. The recesses in the disc can be formed for example simultaneously with the manufacture of the disc itself via an appropriate mould, or may be cut mechanically into the block prepared beforehand. The recesses will then be filled up with the carrier containing the volatile active substance.

Figure 2:
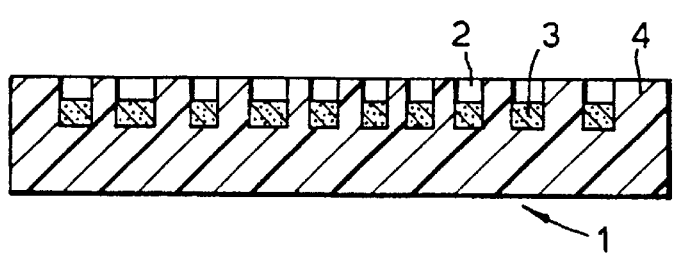
FIG. 2 is a cross section view, along line 11—11, of the device represented in FIG. 1.
Figure 3:
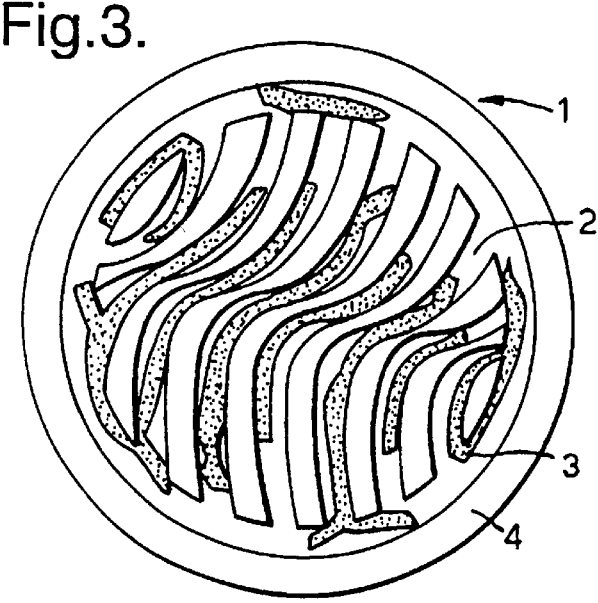
FIG. 3 represents a plan view of the same device once exhausted, i.e. once the perfume has been evaporated.

FIGS. 1 and 2 show a preferred embodiment of the above-described disc (1) having an edge (4) and grooves (2) carved in a wavy form. The disc as shown in FIGS. 1 and 2 can be filled with any appropriate solid carrier material (3), described above and in the Example below and containing any appropriate perfume or other volatile substance, such as those described below in examples 2 to 11. The disc (1) according to the Figures can for example have a diameter of about 7 cm, a thickness of about 17 cm, the grooves (2) having a depth of about 0.5 cm and a width varying between about 0.2 and 0.4 cm. The edge (4) has a width of about 0.5 cm. The amount of solid carrier incorporated and prepared according to any of examples 2 to 11 is from 5 to 7 g, generally about 6 g, resulting in an evaporation surface of from 16 to 20 $cm^2$, and generally about 18 $cm^2$.

When the solid element in the grooves is a material prepared as described in Examples 2 to 11, the diffusion device provides an end point indication when the device becomes inactive, i.e. no longer contains any significant amount of perfume. The material does in fact crack at this point and this is visible to the user and specifically shown in FIG. 3.

EXAMPLE 2

2.23 g of Lithene N4-9000 1OMA and 10.28 g of a perfume base (Splash 115.032 BGE origin: Firmenich SA, Geneva, Switzerland) were manually mixed in an appropriate vessel. 0.34 g of Crodamet 02 were then added under stirring. The fluid mixture was then filled into the recess of a solid support of the invention, such as the one described in Example 1. After about 10 min at room temperature, the resulting polymer oil gelled, encapsulating the perfume base. Gel setting was complete in about half an hour, after which the gel remained set within the casing recesses.

EXAMPLE 3

3.54 g of Lithene® N4-B-1OMA and 6.87 g of a perfume base (Summerfruits 150335F; origin: Firmenich SA, Geneva, Switzerland) were manually mixed in an appropriate vessel until the Lithene® had completely dissolved. In a separate vessel 0.63 g of Jeffamine® D-400 was mixed with 9.79 g of the aforementioned perfume base. The Jeffamine/perfume mixture was then added to the Lithene®/perfume mixture under stirring. 6.25 g of the resulting fluid composition was then filled into the recess of a solid support of the invention (see FIG. 1). After about 30 minutes at room temperature the oil mixture had gelled.

When allowed to stand at ambient temperature the device evaporated >3 g of perfume in 42 days, after which time the gel had cracked.

Similar results were obtained using Green Apple 150123 (origin: Firmenich SA, Geneva, Switzerland) and Tropical 438874 (origin: Firmenich SA, Geneva, Switzerland) as perfume bases, used in the gel at a concentration of 80% w/w.

EXAMPLE 4

3.97 g of Lithene® N4-B-1OMA and 7.71 g of a perfume base (Summerfruits 150335F; origin: Firmenich SA, Geneva, Switzerland) were manually mixed in an appropriate vessel until the Lithene® had completely dissolved. In a separate vessel 0.70 g of a cross-linking mixture (comprising 70.00% w/w Jeffamine® D-400, 11.10% w/w Jeffamine® EDR-148 and 18.90% w/w diethylphthalate) was mixed with 10.98 g of the aforementioned perfume base. The cross-linking/perfume mixture was then added to the Lithene/perfume mixture under stirring. 6.25 g of the resulting fluid composition was then filled into the recess of a solid support of the invention (see FIG. 1). After about 10 minutes at room temperature the oil mixture had gelled.

When allowed to stand at ambient temperature the device evaporated >3 g of perfume in 42 days, after which time the gel had cracked.

EXAMPLE 5

1.44 g of Lithene® N4-9000 1OMA were mixed by hand in a beaker with 14.93 g of a perfume base (Splash 115.032 BGE; origin: Firmenich SA, Geneva, Switzerland), whereupon 0.22 g of Crodamet 02 were added under stirring. The mixture was filled into the recess of a solid casing of the invention of the type as described in Example 1. After 40 min, the mixture gelled. The product was fully cured after approximately 3 h and remained set within in the casing recesses.

EXAMPLE 6

3.70 g of Lithene® N4-B-1OMA and 6.75 g of a perfume base (Peach & Apple 140524; origin: Firmenich SA, Geneva, Switzerland) were manually mixed in an appropriate vessel until the Lithene had completely dissolved. In a separate vessel 0.48 g of Jeffamine® T403 was mixed with 9.97 g of the aforementioned perfume base. The Jeffamine/perfume mixture was then added to the Lithene®/perfume mixture under stirring. 6.25 g of the resulting fluid composition was then filled into the recess of a solid support of the invention (see FIG. 1). After about 25 minutes at room temperature the oil mixture had gelled.

When allowed to stand at ambient temperature the device evaporated >3 g of perfume in 30 days, after which time the gel had cracked.

EXAMPLE 7

2.54 g of Lithene® N4-9000 1OMA and 6.23 g of a perfume base (Terminator 109365B origin: Firmenich SA, Geneva, Switzerland) were mixed by hand and 0.13 g of Crodamet 02 (ratio: Lithene®/Crodamet ca.3:1) were added thereto under stirring. The mixture was filled into the recess of a solid casing of the invention, of the type as described in Example 1. The resulting oil gelled in 15 min at ambient temperature.

EXAMPLE 8

By proceeding as indicated in the previous example but using a molar ratio of Lithene®/Crodamet of 5:1 instead of 3:1, a sticky gel was obtained which lacked a certain degree of rigidity. The mixture was filled into the recess of a solid casing of the invention, of the type as described in Example 1.

EXAMPLE 9

1.87 g of Lithene N4-9000 1OMA were mixed with 5.69 g of a perfume base (Terminator 109365B; origin: Firmenich SA, Geneva, Switzerland), whereupon 0.57 g of Crodamet 02 were added thereto under manual stirring. The mixture was filled into the recess of a solid using of the invention, of the type as described in Example 1. After approximately 20 min at room temperature, the oil gelled.

EXAMPLE 10

Approximately 2 g of Lithene® N4-9000 1OMA were placed in a beaker and mixed with the required amount of a perfume base (Honeysuckle 150061; origin: Firmenich SA, Geneva, Switzerland) until complete solution. The cross-linking agents were pre-mixed and added under stirring to the perfume polymer base. The mixture was filled into the recess of a solid casing of the invention, of the type as described in Example 1.

| % w/w Honeysuckle 150061 | 80.00 | 80.00 | 80.00 | 80.00 |
|---|---|---|---|---|
| % w/w Lithene ® N4-9000 1OMA | 17.14 | 17.49 | 17.85 | 18.24 |
| % w/w Jeffamine ® D-400 | 2.86 | 2.27 | 1.66 | 1.01 |
| % w/w Jeffamine ® EDR-148 | — | 0.24 | 0.49 | 0.75 |
| Gelling time (min) | 59.00 | 33.00 | 21.00 | 7.00 |

EXAMPLE 11

1.55 g of Lithene® N4-9000 1OMA were poured into an appropriate container and mixed with 3.82 g of a perfume base (Lavender de Provence 150060 (origin: Firmenich SA, Geneva, Switzerland) until complete solution.

In a separate beaker, 1.87 of Hycar CTBN 1300×21 (origin: B.F. Goodrich) were dissolved in 4.13 g of the same perfume base, and 5.37 g of this solution were added to the previously obtained perfumed solution of the polymer. The mixture was filled into the recess of a solid casing of the invention, of the type as described in Example 1. A dry and rigid gel formed rapidly at ambient temperature.

What is claimed is:

1. A device for diffusion of an active volatile substance into ambient air or closed spaces, said device comprising a casing or housing and a solid carrier containing said volatile substance, wherein said solid carrier is arranged in at least one recess formed in the casing or housing, said recess having a depth and a width which are chosen in relation to the composition of the solid carrier containing the active substance so that the ratio of the evaporating surface of the solid carrier to the mass of the solid carrier is such that, during the active lifetime of the device, a substantially constant vapour release rate and total evaporation of said active volatile substance are obtained.

2. A device as claimed in claim 1, wherein the casing or housing is formed as a single block.

3. A device as claimed in claim 2, wherein the casing or housing has two faces, one face being flat the and the at least one recess being cut or moulded in the other face thereof.

4. A device as claimed in claim 5 wherein the at least one recess is in the form of a square, a circle, a diamond, a triangle, a star, an oval or a groove.

5. A device as claimed in claim 4 wherein the recess is in the form of a plurality of grooves.

6. A device as claimed in claim 5 wherein the solid carrier comprises several communicating grooves.

7. A device as claimed in claim 1 wherein the solid carrier is made from wood, a mineral material or a synthetic polymer.

8. A device as claimed in claim 7 wherein the solid carrier comprises plaster, glass, acrylic or methacrylic polymers, polystyrene, polyester, a phenolic resin or a silicone resin.

9. A device as claimed in claim 1 wherein the solid carrier containing the volatile substance comprises plaster, silica, carboxymethylcellulose, a stearate, a paraffin, an alginate, a carrageenan, agar-agar, paper, cardboard, a synthetic polymer, a polymer hydrogel or an anhydrous polymer gel.

10. A device as claimed in claim 9, wherein the solid carrier is a synthetic polymer selected from the group consisting of a polyacrylate, a polymethacrylate, a polyurethane, a polyethylene, an ethylene-ethacrylate copolymer, an ethylene-vinyl acetate copolymer, a polyamide and a polyether block amide thermoplastic elastomer.

11. A device as claimed in claim 9, wherein the solid carrier is an anhydrous polymer gel which results from the in situ cross-linking of a functionalised liquid polymer selected from the group consisting of maleinised polybutadiene, maleinised polyisoprene and a copolymer consisting of ethylene and maleic anhydride, with a cross-linking agent which possesses one or more complementary functional groups, in the presence of a perfume, of a deodorizing or sanitizing base or of a surfactant agent.

12. A device as claimed in claim 11 wherein the functionalised polymer is selected from the group consisting of maleinised polybutadiene of MW 5,000–20,000 and maleinised polyisoprene of MW 200,000–500,000.

13. A device as claimed in claim 11 wherein the cross-linking agent is selected from the group consisting of dihydroxypolybutadiene, ethoxylated or propoxylated primary fatty amines, alkylpropyldiamines having an ethoxylated or propoxylated higher aliphatic chain, diethanolamine or diethylenetriamine, and polyoxyalkyleneamines.

14. A device as claimed in claim 13 wherein the cross-linking agent is an oleylamine having 2 ethylene oxide units per molecule, a cocoamine having 5 ethylene oxide units per molecule, or a polyoxy-alkylene-diamine or -triamine.

15. A device as claimed in claim 11, wherein the functionalised liquid polymer and the cross-linking agent are present in a molar proportion of 1:1.

16. A device as claimed in claim 1, wherein the active volatile substance is a perfume, a deodorizing or sanitizing agent or an insect repellent.

17. A device as claimed in claim 1 wherein the at least one recess has a depth of about 0.5 cm and a width of from 0.2 to 0.4 cm.

18. A device as claimed in claim 1 wherein the at least one recess has a surface area of from 10 to 50 $cm^2$.

19. A device as claimed in claim 18 wherein the at least one recess has a surface area of from 16 to 20 $cm^2$.

20. A device as claimed in claim 1 wherein the amount of solid carrier containing the volatile substance at the beginning of the lifetime of the device is from 3 to 30 g.

21. A device as claimed in claim 20 wherein the amount of solid carrier containing the volatile substance at the beginning of the lifetime of the device is from 5 to 10 g.

* * * * *